United States Patent [19]

Pawloski

[11] Patent Number: 4,592,082
[45] Date of Patent: May 27, 1986

[54] QUANTITATIVE DETERMINATION OF MINERAL COMPOSITION BY POWDER X-RAY DIFFRACTION

[75] Inventor: Gayle A. Pawloski, Livermore, Calif.

[73] Assignee: The United States of America as represented by the United States Department of Energy, Washington, D.C.

[21] Appl. No.: 639,287

[22] Filed: Aug. 10, 1984

[51] Int. Cl.[4] .................. G06F 15/46; G06G 7/58; G01N 23/27; G01T 1/36

[52] U.S. Cl. .................. 378/075; 364/498; 378/83

[58] Field of Search .............. 378/75, 45, 76, 83, 378/88, 49, 48, 71, 73; 364/498

[56] References Cited

U.S. PATENT DOCUMENTS

| | | |
|---|---|---|
| 2,897,367 | 7/1959 | Anderman et al. . |
| 3,027,086 | 3/1962 | Hargens, III et al. .............. 364/498 |
| 3,079,499 | 2/1963 | Long ............................. 378/49 |
| 3,102,952 | 9/1963 | Hendee et al. . |
| 3,260,845 | 7/1966 | Duncumb . |
| 3,322,948 | 5/1967 | Baak et al. . |
| 3,428,802 | 2/1969 | Mehta et al. . |
| 3,855,470 | 12/1974 | Sahores et al. ...................... 378/73 |

FOREIGN PATENT DOCUMENTS 55-158545 12/1980 Japan ...................................... 378/73

OTHER PUBLICATIONS

Goehner, R. P., "X-ray Diffraction Quantitative Analysis Using Intensity Ratios and External Standards," vol. 25, p. 309, 1982.

"Quantitative X-ray Diffraction Analysis," *Analytical Chemistry*, vol. 30, No. 2, p. 196, Feb. 1958.

Primary Examiner—Alfred E. Smith
Assistant Examiner—T. N. Grigsby
Attorney, Agent, or Firm—Henry P. Sartorio; Clifton E. Clouse, Jr.; Judson R. Hightower

[57] ABSTRACT

An external standard intensity ratio method is used for quantitatively determining mineralogic compositions of samples by x-ray diffraction. The method uses ratios of x-ray intensity peaks from a single run. Constants are previously determined for each mineral which is to be quantitatively measured. Ratios of the highest intensity peak of each mineral to be quantified in the sample and the highest intensity peak of a reference mineral contained in the sample are used to calculate sample composition.

10 Claims, 1 Drawing Figure

QUANTITATIVE DETERMINATION OF MINERAL COMPOSITION BY POWDER X-RAY DIFFRACTION

BACKGROUND OF THE INVENTION

The U.S. Government has rights in this invention pursuant to Contract No. W-7405-ENG-48 between the U.S. Department of Energy and the University of California, for the operation of Lawrence Livermore National Laboratory.

The invention relates to quantitative analysis of mineral compositions and more particularly to quantitative analysis of mineral compositions by x-ray diffraction.

X-ray diffraction (XRD) is a useful method for identifying mineral content in a sample. Because all minerals have characteristic atomic structures, they can be identified by a unique x-ray diffraction pattern. For any particular mineral, reflections will always occur at certain $2\theta$ angles (which are related to the separation d of parallel planes in the crystal lattice of the mineral by Bragg's Law), and the relative intensities of the reflections will always be in certain ratios to each other. No matter how many other components are in a sample, the presence of any particular mineral can be determined from its characteristic XRD pattern. Thus x-ray diffraction is a powerful tool for qualitative analysis of sample composition. However, because intensities from different minerals vary greatly, a quantitative profile of sample composition is difficult to obtain due to instrument variations and compositional differences.

There are methods for quantitatively determining mineral composition by x-ray diffraction, but these methods generally require knowledge of integrated intensities, densities and absorption properties of the sample. These methods include the (1) pure standard, (2) spiking or dilution, (3) internal standard, (4) standardless, (5) external standard, and (6) matrix flushing methods. None of these methods is ideal. Some require mass absorption coefficients which are difficult to determine and vary with changes in chemical composition. Other methods require time-consuming multiple runs for each mineral, and are often limited to crystalline materials. The methods are also not well adapted to multi-component systems; the maximum number of components accurately measured is limited to four.

Accordingly, it is an object of the invention to provide a quantitative x-ray diffraction method which allows chemical variations of the samples.

It is another object of the invention which can be used routinely, without multiple runs for each mineral.

It is a further object of the invention to provide a method which can handle 5-10 or more minerals at one time.

It is also an object of the invention to provide a method which allows constants to be determined by a simple measurement.

SUMMARY OF THE INVENTION

The invention is an external standard intensity ratio method for quantitatively determining mineralogic compositions of samples by powder x-ray diffraction. The method applies to the quantititative analysis of a sample whose components are selected from a group of known minerals. Prior to the measurement, a constant must be determined for each of the minerals which may be present relative to a reference mineral. X-ray intensity peaks from a single run are then utilized to calculate mineral composition; the ratios of the highest integrated intensity peak of each mineral to be quantified in the sample and the highest integrated intensity peak of the reference mineral in the sample are used in the calculations. The constants are determined from ratios of x-ray lines for standard samples; a standard of known compositions must be made and measured for each component that may be found in the sample. One component of the standard sample is the reference mineral. The constant is obtained from the weight fractions and line intensities, $K = (X_j/X_O)(I_O/I_j)$, where X is the weight fraction and I is the line intensity for component j and for the reference O; for a 1—1 mixture $K = I_O/I_j$. With known K values for all components in a sample, the sample to be quantified is run once, intensities of specific diffraction lines are ratioed, and the weight fractions of all components in the sample are calculated from the equation $\Sigma X_K = 1$. The reference mineral must be present in the test sample; however, if it does not naturally occur in the sample, a quantity of the reference mineral can be added, the measurements performed and the composition corrected for the addition of the reference mineral.

DETAILED DESCRIPTION OF PREFERRED EMBODIMENTS

Figure 1:
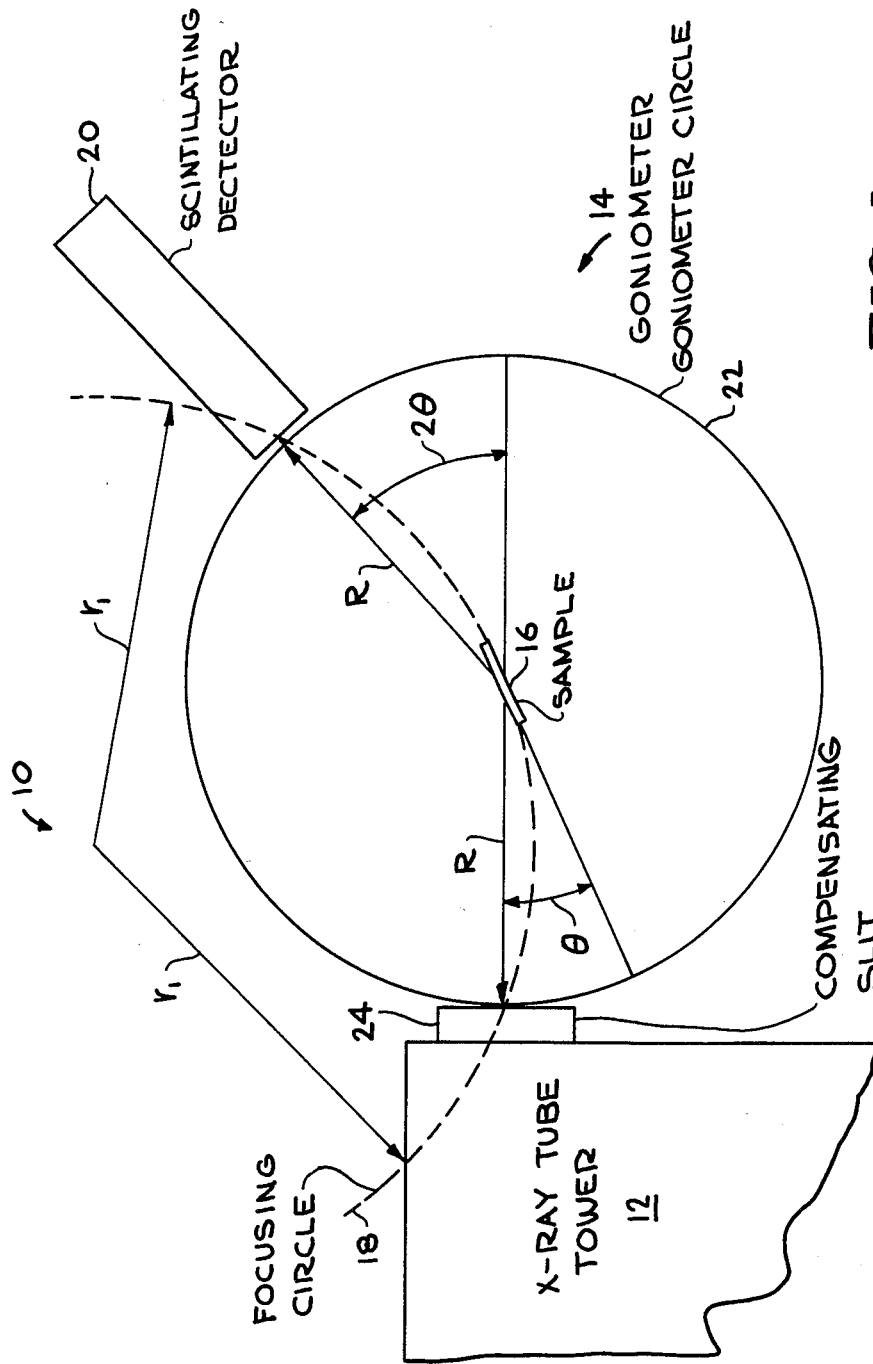
FIG. 1 is a diagrammatic equatorial view of an x-ray diffraction unit utilized in the invention.

A diagrammatic equatorial view of the apparatus for the x-ray diffraction measurements performed according to the invention is shown in FIG. 1. The apparatus 10 includes an x-ray source (not shown) contained in x-ray tube tower 12 and a goniometer 14. A sample 16 is placed tangential to the focusing circle 18 of the goniometer 14. A detector 20 pivots around the sample 16 along goniometer circle 22 during a scan. For parafocusing the sample-detector distance must remain equal throughout the scan. To accomplish this, the sample 16 rotates with one-half the angular velocity of the detector 20, i.e., the sample will be at angle $\theta$ and the detector at angle $2\theta$ to the x-ray source. A theta-compensating slit 24 is utilized with the x-ray source in place of a fixed divergence slit to keep a constant area of the sample irradiated throughout the scan. The theta compensating slit 24 rotates with the sample 16 to maintain constant area of irradiation. In operation a monochromatic beam of radiation from the x-ray source strikes the sample 16 and the reflected intensities are collected or counted by detector 20 as the sample 16 is scanned through a preselected value of the angle $\theta$. As the beam strikes the sample some of the beam is absorbed and some is reflected from the atomic structure; some of the reflected beams reinforce each other as described by Bragg's Law, while at other angles the beams interfere. Thus, a characteristic x-ray diffraction pattern by which a mineral may be identified is obtained.

In one preferred embodiment a copper x-ray tube operating at 45 KeV and 30 MA is utilized. A 1° receiving slit is utilized with detector 20. The x-ray diffraction scans cover the range 2°–45°$2\theta$, automatically stepping 0.04°$2\theta$ every four seconds. The total scan duration is about 73 minutes. Good counting statistics are obtained utilizing this step size and counting speed.

A theta-compensating slit 24 is utilized in the x-ray diffraction apparatus to function as an automatic divergence slit and parallel slit. The theta-compensating slit is utilized in order to keep a constant area of the sample irradiated throughout the scan as opposed to a fixed diversion slit which allows different areas of irradiation as the scan progresses. Because it is difficult to directly obtain comparable intensities, keeping the area of the sample irradiated constant throughout the scan provides that the same x-ray intensity is always on the same amount of sample and makes comparison of intensities easier. More importantly, the theta-compensating slit is utilized to obtain better data at low angles. For some minerals the characteristic x-ray diffraction spectrum occurs at low angles. With a fixed divergence slit, background is high at the beginning of the scan and progressively drops off as the scan continues. With the theta compensating slit, background is relatively constant throughout the scan and low angle peaks are easier to identify. Intensities collected by a compensating slit are not the same as intensities collected by a fixed slit and are not directly comparable.

Optimal particle size of the mineral samples which would not require excessive sample preparation and would yield good x-ray diffraction data was determined to be in the range of about 35 to 45 microns.

The samples are quantified by an external standard intensity ratio method. The weight fractions of two components, (l),(j), are related by $X_j/X_l = K_j(I_j/I_l)$, where $I_j$ is the integrated intensity of a line, preferably the highest intensity peak, of component (j), and $K_j$ is a constant dependent on the geometry of the diffractometer and the nature of component (j). Component (l) is the mineral chosen as the reference mineral. The constants $K_j$ are predetermined from standard samples of each component (j) and component (l). After a set of constants $K_j$ for each component which may be found in the test sample has been obtained, the x-ray diffraction scan of the test sample is performed and the highest intensity peaks of each component (j) is ratioed to the highest intensity peak of component (l). The weight fraction of each component (j) relative to component (l) is determined from the measured intensity ratios and predetermined constants. The weight fraction $X_l$ and the weight fractions $X_j$ for each component (j) can then be determined from the sum of all the weight fractions being equal to 1, $\Sigma X_k = 1$.

One mineral is selected as the reference (component l); this mineral must be present in the test sample, although if it does not naturally occur, a known amount can be added. By using a single mineral as the reference, only one set of constants must be determined. As long as no unknown minerals are found in the test sample, the predetermined set of constants is sufficient. However, new minerals can easily be added by determining an additional constant for the new mineral and adding it to the set of constants. Although a simple measurement of one standard sample (e.g. 1:1 composition) gives a rough value for the constant, a more accurate value is determined by measuring several different standard samples of different weight ratios and determining the slope of the calibration curve, e.g., by a least squares fit method. By choosing a single mineral as the reference, only a single set of constants is necessary. Ideally, this mineral will be present in all test samples. However, even if it is not naturally present, a known amount can be added to a test sample, the augmented test sample can then be analyzed as previously described using the single set of constants, and the composition can then be corrected by normalizing the other weight fractions to add to unity.

The method according to the invention has been applied to samples from the Nevada Test Site. The mineralogic composition of the Nevada Test Site is limited to about 20 minerals, of which 13 are common. Most samples contain 5–10 minerals. Because most of the minerals are found repeatedly, the qualitative analysis is easy. The K constants were calculated for the 13 common minerals by making up standards of each mineral in a 1:1 weight ratio with quartz, which was selected as the reference mineral, because it appears to be present in all samples. The K constant was calculated for each mineral using the highest intensity peak of quartz and the highest intensity peak of each mineral. These K constants were not very accurate. Accordingly, standards of different compositions were prepared and tested to determine the calibration curve for each mineral. K constants were obtained from the slope of the calibration curves, calculated by a least squares fit method, and were more accurate. The K constants for 13 minerals commonly found at Nevada Test site, with quartz as the reference, are shown in Table I.

TABLE I

| Mineral | K constant 1:1 (x) | slope of calibration curve |
| --- | --- | --- |
| Quartz | 1.0000 | 1.0000 |
| Montmorillonite | 23.8202 | 22.0412 |
| Illite | 50.6306 | 30.2904 |
| Clinoptilolite | 12.2582 | 9.7432 |
| Cristobalite | 1.4695 | 1.2940 |
| Feldspars | 1.3267 | 1.2774 |
| Calcite | 0.6790 | 0.6544 |
| Dolomite | 0.4901 | 0.3528 |
| Hornblende | 3.2370 | 2.7698 |
| Kaolinite | 10.5109 | 10.5970 |
| Muscovite | 2.5758 | 1.9180 |
| Biotite | 0.3694 | 0.4304 |

The method was then tested on samples with 3-11 components, and found to be accurate to ±7.0 wt %. The minimum amount of each of the minerals that could be detected by x-ray diffraction was also determined, and ranged from 7 wt % to as low as 0.5 wt % (with the exception of glass). The minimum amounts of minerals detectable are shown in Table II. (Glass is an amorphous material rather than a mineral but was included because it is sometimes present.)

TABLE II

| Quartz | 0.5 wt % |
| --- | --- |
| Montmorillonite | 5.0 |
| Illite | 7.0 |
| Clinoptilolite | 5.0 |
| Cristobalite | 1.0 |
| Feldspars | 2.0 |
| Calcite | 0.5 |
| Dolomite | 0.5 |
| Glass | 40.0 |
| Hornblende | 2.0 |
| Kaolinite | 5.0 |
| Muscovite | 3.0 |
| Biotite | 5.0 |

The process has been implemented using a computer code written to calculate the mineral contents as previously described. The K constants of all minerals are stored in the computer. The measured ratios of the highest intensity peak of each mineral present to the highest intensity peak of the reference mineral (quartz)

are input to the computer, the code is run, and a report is produced.

The invention provides an improved external standard method for quantitatively determining mineralogic or other composition of a sample by X-ray diffraction. The invention is easy to implement, sample preparation is quick, analysis equipment is automated, and run time for each sample is short. The method is particularly applicable to analysis of samples from the Nevada Test Site where mineral composition is limited; however, the method can be extended to the analysis of any composition as long as the standard coefficients for the minerals which may be present in the test sample can first be determined. These standards must be made with one common mineral which will be found in every test sample. However, if the reference mineral does not naturally occur in the sample, it can be added and the results then corrected. Once the standard coefficients are determined they may be stored in a computer program, and summary reports routinely generated from measured input data. Additional elements can easily be added.

Changes and modifications in the specifically described embodiments can be carried out without departing from the scope of the invention which is intended to be limited only by the scope of the appended claims.

I claim:

1. A method of quantitatively determining the mineral composition in a test sample containing a number (m) of minerals from a group (n) of known minerals, wherein n=13, where m≦n, by x-ray diffraction, comprising:

determining from standard samples of the known minerals a set of (n) standard coefficients $K_j = (X_j/X_l)(I_l/I_j)$ for each mineral (j=2 ... n) in the group of known minerals (j=2 ... n) relative to one mineral (l) in the group selected as a reference mineral, where X is the weight fraction of the mineral in a standard sample, and I is the x-ray integrated intensity peak of each mineral obtained from the standard sample;

obtaining an x-ray diffraction pattern of the test sample;

indentifying each of the (m) minerals in the test sample for the x-ray diffraction pattern;

calculating the relative weight fractions $X_j/X_l$ for each mineral (j=2 ... m) compared to the reference mineral (l) from the ratio of the measured highest integrated intensity peak $I_j$ of each mineral in the test sample to the measured highest integrated intensity peak $I_l$ of the reference mineral in the test sample, and from the previously determined standard coefficients, $X_j/X_l = K_j(I_j/I_l)$; and calculating the weight fraction of the reference mineral $X_l$, and the weight fractions $X_j$ of each mineral (j=2 ... m) from the condition that the sum of the weight fractions is 1, $\Sigma X_i = 1$ (i=1 ... m).

2. The method of claim 1 wherein the test sample does not contain the reference mineral, further comprising the steps of:

adding a known amount of the reference mineral to the test sample; and normalizing the calculated weight fractions of the minerals to correct for the amount of reference mineral added.

3. The method of claim 1 wherein the reference mineral is quartz.

4. The method of claim 2 wherein the reference mineral is quartz.

5. The method of claim 1 wherein the step of obtaining the x-ray diffraction pattern of the test sample is performed using a goniometer having a theta compensating slit to keep a constant area of the sample irradiated during a scan.

6. The method for claim 5 wherein the scan covers the range $2°-45°2\theta$.

7. The method of claim 6 wherein the scan is performed in steps of $0.04°2\theta$ every 4 seconds.

8. The method of claim 1 wherein the standard coefficients are determined from a measured calibration curve of each mineral relative to the reference mineral.

9. The method of claim 8 wherein the standard coefficients are determined by a least squares fit of the measured values for a number of different weight ratios.

10. A method of quantitatively determining the mineral composition in a test sample containing a number (m) of minerals from a group (n) of known minerals, where m≦n, by x-ray diffraction, comprising:

determining from standard samples of the known minerals a set of (n) standard coefficients $K_j = (X_j/X_l)(I_l/I_j)$ for each mineral (j=2 ... n) in the group of known minerals (j=2 ... n) relative to one mineral (l) in the group selected as a reference mineral, where X is the weight fraction of the mineral in a standard sample, and I is the x-ray integrated intensity peak of each mineral obtained from the standard sample;

obtaining an x-ray diffraction pattern of the test sample using a goniometer having a theta compensating slit to keep a constant area of the sample irradiated during a scan, wherein the scan covers the range $2°-45° 2\theta$ and is performed in steps of $0.04° 2\theta$ every 4 seconds;

indentifying each of the (m) minerals in the test sample for the x-ray diffraction pattern;

calculating the relative weight fractions $X_j/X_l$ for each mineral (j=2 ... m) compared to the reference mineral (l) from the ratio of the measured highest integrated intensity peak $I_j$ of each mineral in the test sample to the measured highest integrated intensity peak $I_l$ of the reference mineral in the test sample, and from the previously determined standard coefficients, $X_j/X_l = K_j(I_j/I_l)$; and calculating the weight fraction of the reference mineral $X_l$, and the weight fractions $X_j$ of each mineral (j=2 ... m) from the condition that the sum of the weight fractions is 1, $\Sigma X_i = 1$ (i=1 ... m).1

* * * * *